United States Patent [19]

Glass

[11] Patent Number: 5,162,348
[45] Date of Patent: Nov. 10, 1992

[54] TREATMENT OF CYSTIC FIBROSIS

[75] Inventor: Mitchell Glass, Wilmington, Del.

[73] Assignee: Imperial Chemical Industries PLC, London, England

[21] Appl. No.: 528,656

[22] Filed: May 24, 1990

[51] Int. Cl.$^5$ ............................................. A61K 31/41
[52] U.S. Cl. .................................................... 514/359
[58] Field of Search ........................................ 514/359

[56] References Cited

FOREIGN PATENT DOCUMENTS

| | | |
|---|---|---|
| 0189305 | 1/1986 | European Pat. Off. |
| 0276101 | 1/1988 | European Pat. Off. |
| 0291234 | 5/1988 | European Pat. Off. |
| 0337704 | 4/1989 | European Pat. Off. |
| 0345906 | 6/1989 | European Pat. Off. |
| 0369391 | 11/1989 | European Pat. Off. |
| 0402068 | 6/1990 | European Pat. Off. |
| WO86/00077 | 1/1986 | PCT Int'l Appl. |

OTHER PUBLICATIONS

Berger, et al., Complement Receptor Expression on Neutrophils at an Inflammatory Site, the Pseudomonas-infected Lung in Cystic Fibrosis, *J. Clin Invest.* (1989), 84, 1302–1313.

Sommerhoff, C. P. et al., Neutrophil Elastase and Cathepsin G. Stimulate Secretion from Cultured Bovine Airway Gland Serous Cells, *J. Clin. Invest.* (1990), 85, 682–689.

Sommerhoff, C. E. et al. Neutrophil Proteases Stimulate Secretion of $^{35}$S-labeled Glycoconjugates from Cultured Bovine Tracheal Gland Serous Cells, *Faseb J.* (1989) 3, A534, Abstract 1791.

Suter, S., The Imbalance Between Granulocyte Neutral Proteases and Antiproteases in Bronchial Secretions from Patients with Cystic Fibrosis; In Hoiby N, Pedersen SS, Shand GH, Doring G, Holder IA (eds): *Pseudomonas aeruginosa* Infection. Antibiot Chemother. Basel, Karger, 1989, vol. 42. pp. 158–168.

*Primary Examiner*—S. J. Friedman
*Attorney, Agent, or Firm*—Thomas E. Jackson

[57] ABSTRACT

There is provided a novel therapeutic product for use in the symptomatic treatment of cystic fibrosis and for use in the manufacture of a medicament for the treatment of cystic fibrosis, as well as a method for treatment of cystic fibrosis with the therapeutic product and a method of treatment of cystic fibrosis with the therapeutic product in combination with one or more other agents indicated for the treatment of cystic fibrosis.

3 Claims, No Drawings

TREATMENT OF CYSTIC FIBROSIS

This invention describes a novel therapeutic product and, more particularly, the use of 4-(4-chlorophenylsulphonylcarbamoyl)-benzoyl-L-valyl-L-proline 1(RS)-(1-trifluoroacetyl-2-methylpropyl)-amide, or a pharmaceutically acceptable salt thereof, in the symptomatic treatment of cystic fibrosis. (Although the therapeutic product is named here as 1(RS), the invention described herein includes any ratio of the 1(R)- and 1(S)-isomers of the above named compound, or the pharmaceutically acceptable salts thereof.)

Cystic fibrosis is an inherited form of chronic bronchitis with mucus hypersecretion, generally accompanied by poor clearance of the airway secretions, obstruction of airflow and chronic bacterial infection of the airways, commonly by *Pseudomonas aeruginosa*. It is known that the sputum and bronchoalveolar lavage fluid from cystic fibrosis patients reduce the ability of neutrophils to take up and kill *P. aeruginosa*.

Accordingly, the present invention provides a novel therapeutic product for use in the treatment of cystic fibrosis in a mammal, especially a human, in need thereof which product comprises 4-(4-chlorophenylsulphonylcarbamoyl)benzoyl-L-valyl-L-proline 1(RS)-(1-trifluoroacetyl-2-methylpropyl)amide, or a pharmaceutically acceptable salt thereof.

As a further aspect of the invention, there is provided the use of 4-(4-chlorophenylsulphonylcarbamoyl)benzoyl-L-valyl-L-proline 1(RS)-(1-trifluoroacetyl-2-methylpropyl)amide, or a pharmaceutically acceptable salt thereof, for the manufacture of a medicament for the treatment of cystic fibrosis.

As another aspect of the invention, there is provided a method of treatment of cystic fibrosis in a mammal, especially a human, in need thereof with 4-(4-chlorophenylsulphonylcarbamoyl)-benzoyl-L-valyl-L-proline 1(RS)-(1-trifluoroacetyl-2-methylpropyl)amide, or a pharmaceutically acceptable salt thereof.

As yet another aspect of the invention, there is provided a method of symptomatic treatment of cystic fibrosis with 4-(4-chlorophenylsulphonylcarbamoyl)-benzoyl-L-valyl-L-proline 1(RS)-(1-trifluoroacetyl-2-methylpropyl)amide, or a pharmaceutically acceptable salt thereof, in combination with one or more other agents indicated for the treatment of cystic fibrosis. Such agents include, but are not limited to, antibiotics, bronchodilators, corticosteroids, oxygen, mucolytics, and mucorheologic agents, including aerosolized amiloride.

Suitable pharmaceutically acceptable salts of 4-(4-chlorophenylsulphonylcarbamoyl)benzoyl-L-valyl-L-proline 1(RS)-(1-trifluoroacetyl-2-methylpropyl)amide (hereafter referred to as "the Compound") include, for example, those described in U.S. Pat. No. 4,910,190, for example, alkalai metal and alkaline earth metal salts (such as sodium, potassium, calcium or magnesium salts), ammonium salts, and salts with organic bases affording a pharmaceutically acceptable cation. A preferred salt of the Compound for use for treatment of cystic fibrosis is, for example, a sodium or potassium salt.

The Compound and its production are described in U.S. Pat. No. 4,910,190 where it was referred to as 3(RS)-[4-[(4-chlorophenyl)sulfonylaminocarbonyl]-phenylcarbonyl]-L-valyl-N-[3-(1,1,1-trifluoro-4-methyl-2-oxopentyl)]-L-prolinamide, but the name given hereinabove is now preferred. It is noted that Dess-Martin periodinane, described as the preferred oxidant and used in the final step for the production of the Compound in Examples 104 and 121, may in certain circumstances constitute an explosive hazard. Accordingly, it may be preferred to use an alternative oxidant for preparing the ketone from the corresponding alcohol. Alternative methods which may be useful include the use of oxalyl chloride, dimethyl sulfoxide and a tertiary amine (with the best results being obtained with 10-20 equivalents of oxidizing agent); the use of acetic anhydride and dimethyl sulfoxide; the use of chromium trioxide pyridine complex in methylene chloride; and the use of alkaline potassium permanganate solution. For example, the Compound may be obtained from the corresponding alcohol in approximately 60% yield using two equivalents of the latter oxidant.

In use, the Compound will generally be administered for symptomatic treatment of cystic fibrosis in the form of a conventional pharmaceutical composition, for example, as generally described in U.S. Pat. No. 4,910,190, and preferably as an aerosol. A formulation providing a solution containing a concentration of 10 mg/mL of the Compound and suitable for use with a nebulizer or as an injectable solution is described below in Example 1. A suitable nebulizer for use is, for example, a RETEC (trademark) nebulizer, in which the solution is nebulized with compressed air.

In general, the therapeutic product will be administered to humans at a daily dose in the range of, for example, 5 to 100 mg of the Compound by aerosol or 50 to 1000 mg intravenously, or a combination of the two. However, it readily will be understood that it may be necessary to vary the dose of therapeutic product administered in accordance with well known medical practice to take account of the nature and severity of the cystic fibrosis under treatment, concurrent therapy, and the age, weight and sex of the patient receiving treatment. It similarly will be understood that generally equivalent amounts of a pharmaceutically acceptable salt of the Compound also may be used.

The utility of the Compound, or a pharmaceutically acceptable salt thereof, in the symptomatic treatment of cystic fibrosis may be demonstrated using standard clinical study protocols, for example as described below in Study A and Study B, in which improvement in clinical or biochemical parameters may be measured.

Study A in cystic fibrosis is a randomized, double blind, parallel study in 10 to 20 adult patients assigned to receive 35 mg/day of the Compound or vehicle (placebo) to be administered by aerosol inhalation for two to three weeks. A formulation as described in Example 1 may be used for the treatment group, and a similar formulation without the Compound for the vehicle (control) group. The RETEC (trademark) nebulizer is filled with approximately 3.5 mL of the study medication or vehicle (control), as appropriate. The solution in the nebulizer is nebulized with compressed air. The patient breathes normally (tidal volume) for eight minutes with the nebulizer in his mouth. Clinical endpoints include sputum production, spirometry and peak flow, using standard clinical methods in accord with American Thoracic Society standards. Improvements in clinical variables, such as symptoms (using diary cards), sputum production, $FEV_1$ (forced expiratory volume in one second), and FVC (forced vital capacity), are determined by standard methods of statistical analysis.

Study B in cystic fibrosis is a randomized, double-blind, parallel study in 10 to 20 adult patients assigned to receive the Compound administered at 350 mg/day (for example, 35 mL of the formulation of Example 1) or a corresponding amount of vehicle (placebo) by intravenous infusion for 3 to 4 days, followed by aerosol inhalation at 35 mg/day for 2-3 weeks (as described in Study A). Bronchoalveolar lavage is performed at the start of the study and at the completion of the intravenous and aerosol phases. Clinical variables examined include symptoms, sputum production, spirometry and peak flow, measured and analyzed as described for Study A. Biochemical studies include measurements of bronchoalveolar lavage fluid activity on neutrophil phagocytosis and killing of P. aeruginosa, analyzed by standard methods.

The following non-limiting Example illustrates a typical formulation of the Compound for use in the method of treatment provided by the invention.

EXAMPLE 1

This example provides a formulation for 4-(4-chlorophenylsulphonylcarbamoyl)benzoyl-L-valyl-L-proline 1(RS)-(1-trifluoroacetyl-2-methylpropyl)amide, listed as a THERAPEUTIC PRODUCT, which provides a strength of 10 mg/mL in phosphate-buffered saline and is suitable for a nebulizer solution or for an injectable solution. A corresponding PLACEBO formulation is also provided. The prepared solutions are preferably sealed in ampules of a convenient size, for example 5 mL, and stored with refrigeration until use.

| INGREDIENT | WEIGHT PER mL | |
|---|---|---|
| | 10.0 mg | PLACEBO |
| THERAPEUTIC PRODUCT (1) | 10.0 mg | — |
| Dibasic Sodium Phosphate, Heptahydrate, USP | 11.97 mg | 10.74 mg |
| Monobasic Sodium Phosphate, Monohydrate, USP | 0.74 mg | 1.25 mg |
| Sodium Chloride, USP | 4.50 mg | 5.48 mg |
| 1N Sodium Hydroxide Solution or 0.05M Monobasic Sodium Phosphate Solution (2) | q.s. | q.s. |
| Water for Injection, USP q.s. ad | 1.0 mL (1.01 gm) | 1.0 mL (1.01 gm) |

(1) The nominal concentration of THERAPEUTIC PRODUCT in this formulation is 10 mg/mL. A manufacturing adjustment is made for the drug substance purity.
(2) Added to adjust pH to 7.0–7.5

MANUFACTURING DIRECTIONS: THERAPEUTIC PRODUCT

1. Charge approximately 90% of the required amount of Water for Injection, USP to a vessel equipped with a suitable agitation device, and connected to a heater/cooler circulation bath.
2. Adjust the temperature of the circulation bath to 30° C.
3. Charge with continuous stirring, the required amount of Dibasic Sodium Phosphate, Heptahydrate, USP and continue stirring until dissolved.
4. Charge very slowly with continuous stirring the required amount of THERAPEUTIC PRODUCT.
5. Continue to stir for approximately 30 minutes until dissolved, then decrease the temperature of the circulation bath to 25° C.
6. Charge with continuous stirring the required amount of Monobasic Sodium Phosphate, Monohydrate, USP and continue stirring until dissolved.
7. Charge with continuous stirring the required amount of Sodium Chloride, USP and continue stirring until dissolved.
8. Measure the pH and adjust to 7.0 to 7.5 with 1N Sodium Hydroxide Solution or 0.05M Monobasic Sodium Phosphate Solution, if necessary.
9. Bring the batch to final weight (calculated from specific gravity of 1.01) with Water for Injection, USP.
10. Aseptically filter the bulk solution into a suitable, sterilized filling vessel. Aseptically fill and seal the ampules.
11. Leak test ampules and visually inspect for particulate matter and other defects.

MANUFACTURING DIRECTIONS: PLACEBO

The procedure listed above is carried out with the omission of steps 2, 4 and 5, and without the need for temperature control.

What is claimed is:

1. A method of treatment of cystic fibrosis in a mammal, especially a human, in need thereof comprising administering to said mammal an effective amount of 4-(4-chlorophenylsulphonylcarbamoyl)benzoyl-L-valyl-L-proline 1(RS)-(1-trifluoroacetyl-2-methylpropyl)amide, or a pharmaceutically acceptable salt thereof.

2. A method as claimed in claim 1 wherein the pharmaceutically acceptable salt is selected from the group consisting of alkalai metal and alkaline earth metal salts, ammonium salts, and salts with organic bases affording a pharmaceutically acceptable cation.

3. A method as claimed in claim 2 wherein the pharmaceutically acceptable salt is a sodium or potassium salt.

* * * * *